United States Patent
Usai et al.

(10) Patent No.: US 12,226,215 B2
(45) Date of Patent: Feb. 18, 2025

(54) CONDUCTIVE POLYMERIC COMPOSITION AND METHOD FOR PREPARING THE CONDUCTIVE POLYMERIC COMPOSITION

(71) Applicants: ALMA MATER STUDIORUM—UNIVERSITA' DI BOLOGNA, Bologna (IT); UNIVERSITA' DEGLI STUDI DI CAGLIARI, Cagliari (IT); Giuseppe Arnaldo Usai, Rome (IT)

(72) Inventors: Giuseppe Arnaldo Usai, Rome (IT); Erika Scavetta, Bologna (IT); Isacco Gualandi, Bologna (IT); Beatrice Fraboni, Bologna (IT); Marta Tessarolo, Bologna (IT); Annalisa Bonfiglio, Cagliari (IT); Danilo Pani, Cagliari (IT); Eleonora Sulas, Cagliari (IT)

(73) Assignees: Giuseppe USAI, Rome (IT); ALMA MATER STUDIORUM—UNIVERSITA' DI BOLOGNA, Bologna (IT); UNIVERSITA' DEGLI STUDI DI CAGLIARI, Cagliari (IT)

( * ) Notice: Subject to any disclaimer, the term of this patent is extended or adjusted under 35 U.S.C. 154(b) by 510 days.

(21) Appl. No.: 17/607,313

(22) PCT Filed: Apr. 29, 2020

(86) PCT No.: PCT/IB2020/054018
§ 371 (c)(1),
(2) Date: Oct. 28, 2021

(87) PCT Pub. No.: WO2020/222130
PCT Pub. Date: Nov. 5, 2020

(65) Prior Publication Data
US 2022/0202333 A1 Jun. 30, 2022

(30) Foreign Application Priority Data
Apr. 29, 2019 (IT) ............... 102019000006437

(51) Int. Cl.
*A61B 5/268* (2021.01)
*A61B 5/256* (2021.01)
(Continued)

(52) U.S. Cl.
CPC .............. *A61B 5/268* (2021.01); *A61B 5/256* (2021.01); *C08G 61/126* (2013.01);
(Continued)

(58) Field of Classification Search
CPC ........ C08K 5/3445; C08K 5/098; C08K 5/42; C08L 65/00
See application file for complete search history.

(56) References Cited

U.S. PATENT DOCUMENTS

| | | | |
|---|---|---|---|
| 2008/0139710 A1* | 6/2008 | Tsukada | C08J 3/09 524/100 |
| 2012/0043530 A1* | 2/2012 | Badre | C08J 5/18 257/40 |
| 2018/0014780 A1* | 1/2018 | Sotzing | A61B 5/25 |

FOREIGN PATENT DOCUMENTS

| | | |
|---|---|---|
| JP | 2006257148 A | 9/2006 |
| JP | 2015077226 A | 4/2015 |

(Continued)

OTHER PUBLICATIONS

Teo et al., "Highly Stretchable and Highly Conductive PEDOT:PSS/Ionic Liquid Composite Transparent Electrodes for Solution-Processed Stretchable Electronics" ACS Appl. Marer. Interfaces, 2017, v 9, p. 819-826.

(Continued)

*Primary Examiner* — Jacob T Minskey
*Assistant Examiner* — Adrien J Bernard
(74) *Attorney, Agent, or Firm* — Gregory P. Einhorn; Greer, Burns & Crain, Ltd.

(57) ABSTRACT

The invention provides a composition for a conductive polymeric material suitable for the production of electrodes for recording electrophysiological signals, such as electrocardiogram (EGG), electromyogram (EMG), electroencephalogram (EEG), etc., and signals related to the impedance variation of the body or skin, both deriving from active and passive measures (for example, breathing, electrodermal response, etc.). For this purpose a formulation containing FEDOT and ionic liquids has been developed. The formulation according to the invention can be used generically in the context of detecting bioelectric signals and can be applied on wearable items, in particular in fabric, such as for example garments of different shapes, so as to be in direct contact with the areas of the body subject to detection. The artifacts include diving artefacts, such as watertight suits, and for water sports and submarine surveys, artifacts used in the medical and health sector such as plasters, elastic support bands and adhesive support bands and textile articles, including special fabrics such as bioceramics.

26 Claims, 11 Drawing Sheets

(51) Int. Cl.
| | | |
|---|---|---|
| | *C08G 61/12* | (2006.01) |
| | *C08K 5/3445* | (2006.01) |
| | *C08K 5/41* | (2006.01) |
| | *C09D 5/24* | (2006.01) |
| | *C09D 7/63* | (2018.01) |
| | *C09D 11/102* | (2014.01) |
| | *C09D 11/52* | (2014.01) |
| | *C09D 165/00* | (2006.01) |

(52) U.S. Cl.
CPC .............. *C08K 5/3445* (2013.01); *C08K 5/41* (2013.01); *C09D 5/24* (2013.01); *C09D 7/63* (2018.01); *C09D 11/102* (2013.01); *C09D 11/52* (2013.01); *C09D 165/00* (2013.01); *C08G 2261/12* (2013.01); *C08G 2261/148* (2013.01); *C08G 2261/3326* (2013.01); *C08G 2261/3342* (2013.01); *C08G 2261/514* (2013.01); *C08G 2261/792* (2013.01); *C08G 2261/94* (2013.01)

(56) References Cited

FOREIGN PATENT DOCUMENTS

| | | |
|---|---|---|
| JP | 2016000363 A | 1/2016 |
| WO | 2016007746 A1 | 1/2016 |

OTHER PUBLICATIONS

Trinidade et al., "High electrical conductance poly(3,4-ethylenedioxythiophene) coatings on textile for electrocardiogram monitoring" Synthetic Metals, 2015, v 210, p. 179-185.

* cited by examiner 1-ethyl-3-methylimidazolium chloride 1-butyl-3-methylimidazolium bromide 1-butyl-3-methylimidazolium acetate 1-ethyl-3-methylimidazolium acetate 1-ethyl-3-methylimidazolium tosylate 1-methyl-3-propylimidazolium iodide 1-decyl-3-methylimidazolium chloride

CONDUCTIVE POLYMERIC COMPOSITION AND METHOD FOR PREPARING THE CONDUCTIVE POLYMERIC COMPOSITION

This application is a national phase application claiming benefit of priority under 35 U.S.C. § 371 to Patent Convention Treaty (PCT) International Application serial number PCT/IB2020/054018, filed Apr. 29, 2020, now pending, which claims the benefit of priority to Italian patent No. 102019000006437 filed on Apr. 29, 2019. The aforementioned applications are expressly incorporated herein by reference in their entirety and for all purposes.

TECHNICAL FIELD

The present invention relates to a conductive polymeric composition which can be used, for example, for the production of electrodes for recording bioelectric signals.

More specifically, the invention relates to the construction of new textile electrodes for recording bioelectric signals based on conductive polymers added with ionic liquids.

More precisely, the present invention allows to obtain a conductive polymeric composition for the production of electrodes printed directly on fabric (for example: bioceramics, cotton, nylon) and which can be integrated in wearable clothing and/or articles.

Said electrodes have a low skin/electrode impedance such as to make it possible to record bioelectric signals, such as the electrocardiogram (ECG), without using an electrolytic gel or hydrating them with the addition of water or saline solution or natural body sweating. These electrodes are also suitable for bioimpedance measurements, being suitable also for injecting alternating currents of low entity as required by this type of application (e.g. breath measurement or electrodermal response).

The electrodes made with the composition of the invention, applied with techniques of printing on fabric, allow to detect with high accuracy and precision bioelectrical parameters such as the ECG trace of the subject wearing the garment and the respiratory activity of the same.

The technical problem that these electrodes solve is, among others, the resistance to washing, so that the textile products and/or clothing on which these electrodes are applied can be washed several times without the electrodes losing their electrical conduction characteristics.

PRIOR ART

The first examples of textile electrocardiogram electrodes date back to the early 2000s, when numerous projects were funded in order to develop functionalized clothing so that vital parameters could be monitored in real time.

However, the materials initially used for the realization of these electrodes were made of stainless steel wire mesh sewn inside fabrics, absolutely unsuitable to be worn because of their mechanical properties which are scarcely compatible with the fabrics in which they were to be integrated, in terms of elasticity, density and hardness, making their presence inside the garment uncomfortable. Subsequent developments in technologies have led to the production of threads of non-conductive textile material covered (coated) with particles of conductive material, such as silver, creating conductive and soft to the touch yarns. However, these electrodes have an excessive electrode-skin contact impedance for dry use, therefore requiring the use of an electrolytic gel capable of improving the contact between the metallic conductor and the skin from an electrical point of view. Furthermore, the adoption of these electrodes in a sensorized garment requires that the yarn include these conductive fibers at the time of manufacture, or that conductive patches made with these materials are applied (sewn or glued) on the base fabric, making the production process more complex and not allowing a seamless approach, necessary in various areas.

These problems have been partially solved by making the electrodes with intrinsically conductive polymers such as for example the PEDOT:PSS (https://en.wikipedia.org/wiki/PEDOT:PSS) which, being light, flexible and soft, are easily integrated inside a garment for non-invasive control of vital signs. Although the industrial applications of the PEDOT mainly involve its macromolar salt with polystyrene sulphonate (PSS), the literature reports other anions used in combination with the PEDOT such as perchlorate, tetrafluoroborate, hexafluorophosphate, nitrate, sulphate, chloride, tosylate, sulphonamides with fluorinated substituents such as bis (trifluoromethyl)sulphonyl-amide, bis-(perfluoroethyl)sulphonyl-amide, bis-(heptafluoro-propinyl)sulphonyl-amide and bis-(nonafluoro-butinyl)sulphonyl-amide and sulphonates with fluorinated substituents, such as triflate, nonafluorobuthane sulphonate and heptadecafluoroethane sulphonate (PEDOT, Principles and Applications of an intrinsically conductive polymer, Andreas Elschner, Stephan Kirchmeyer, Wilfried Lövenich, Udo Merker, Knied Reuter, Taylor and Francis, 2011; Anal. Bioanal. Chem. (2013) 405: 509-532). Numerous examples of textile electrodes for the electrocardiogram have been made with PEDOT:PSS since 2015 (Conf. Proc. IEEE Eng. Med. Biol. Soc. 2015; 2015: 3197-200; IEEE TRANSACTIONS ON BIOMEDICAL ENGINEERING, VOL. 63, NO. 3, MARCH 2016; Computing in Cardiology 2017, VOL 44, 129-422; IEEE SENSORS JOURNAL, VOL. 18, NO. 10, MAY 15, 2018, 4097-4107; ACS Appl. Mater. Interfaces 2017, 9, 37524-37528; Sensors 2018, 18, 3890; Scientific Reports|5: 15003; Synthetic Metals 210 (2015) 179-185; Bio Med EngOnLine (2018) 17:38). Similarly, document US2018/014780 describes an advanced methodology for preparing conductive fabrics based on conductive polymers and nucleophilic nanoparticles, but does not provide for the presence of ionic liquids. The fabrics obtained have good electrical conductivity, and are used for various applications including electrocardiogram electrodes. However, the electrodes thus obtained have a good skin/electrode impedance only when they are wet or used with the help of an electrolytic gel, for example when applied to wet skin.

These electrodes have superior performance with respect to metallic materials as they have both ionic and electronic conductivity, which should make it possible to convert the bioelectric (ionic) signal into a form readable by the reading electronics which is based on electronic currents. Despite this, the high impedance values of the skin/electrode interface, combined with the dehydration process of the PEDOT:PSS, make it necessary to add an electrolyte that allows the skin to hydrate (in the absence of natural sweat) and improve the contact before use.

This electrolyte, which must be applied on the electrodes, in some formulations can lead to skin irritation in sensitive subjects and in any case renders uncomfortable the use of the clothes thus made and does not make them applicable in everyday life. At the same time the hydration of the electrode with saline solution wets the garment, making it uncomfortable, and does not represent a stable solution over time, given the natural tendency to evaporation. In part, these problems could be overcome in the presence of a body sweat capable of allowing sufficient hydration of the electrode, but this severely limits its applications to specific fields of interest, such as the recording of bioelectric signals in people who are carrying out physical activity.

In order to improve the application of these electrodes and extend it to subjects who do not sweat, it is necessary to identify constructive solutions that allow to overcome the need to add an external electrolyte in the form of gel or liquid. Malliaras et al. (*J. Mater. Chem. C*, 2015, 3, 8942-8948; *Adv. Healthcare Mater.* 2014, 3, 1377-1380) have proposed to use an additional layer of ionic gel made on the surface of the electrode in PEDOT:PSS. In this way the electrode must be built through two printing processes; a first phase in which the PEDOT:PSS electrode is deposited on the fabric, followed by a second step in which the ionic gel is deposited on the previously made electrode. The ionic gel is an additional layer that must be placed on the surface of the electrode and its application also requires a further passage of illumination with a UV lamp to obtain photo-induced cross-linking of its components; moreover the ionic liquid used for the realization of the gel was inserted among the carcinogenic compounds.

The application of a layer of solid hydrogel, based on non-toxic salts, such as sodium chloride or potassium chloride, is also the basis of the pre-gelled disposable electrodes normally used in clinical practice. The adhesiveness of these preparations, given by the aqueous base and necessary to hold the electrode in position during the measurement, tends to decrease over time, with a worsening of the conditions (life-time of the open package typically <72 hours). Furthermore, a hydrogel of this type, in addition to complicating, as mentioned, the production process, does not lend itself adequately to the application of sensorized clothing due to the reduction of comfort for the subject. Not to mention the unacceptable lack of washing robustness, which affects the constancy over time of the electrochemical characteristics of the sensor. As part of the same course, JP2015077226A and JP2016000363A are mentioned.

JP2015077226A describes a system consisting of textile electrodes obtained by successive impregnation phases of the fabric with polymer and ionic liquids, which however are not incorporated in a single formulation. JP2016000363A describes a process for applying electrodes on manufactured articles which, however, involves the deposition of successive layers of different materials. In this document no mention is made of the theme of washing, but it is explicitly stated that, to protect the electrode, an additional protective layer is applied, which therefore provides for a further manufacturing step.

Room temperature ionic liquids are salts that have melting points below 100° C. Some examples of ionic liquids are: ethylammonium nitrate, 1-butyl-3-methyl imidazolium-tetrafluoroborate and 1-butyl-3-methyl-imidazolium bis (trifluoromethyl-sulphonyl)-imide. Ionic liquids are characterized by low vapor pressure, moderate electrical conductivity, thermal stability and a large electrochemical window.

The combination of ionic liquids and PEDOT:PSS has been proposed in some publications (*J. Mater. Chem.*, 2008, 18, 5354-5358; *ACS Macro Lett.* 2017, 6, 473-478; *Macromolecules* 2015, 48, 8989-8997) as practical examples of chemical synthesis and for the control of the chemical-physical properties of the polymer (*Adv. Mater.* 2016, 28, 8625-8631; *Chem. Mater.* 2007, 19, 2147-2149). Furthermore, the properties of these materials have been exploited for some real applications, such as the realization of organic electrochemical transistors (Wu et al. *Adv. Mater.* 2018, 1805544), field effect transistors (Wang et al., *Sci. Adv.* 2017; 3:1602076), of gas sensors (CN103233256), electrochemical sensors (CN20121115258) and transparent and flexible electrodes for the production of displays (WO2018171317). For example, US2012/043530 describes compositions based on PEDOT:PSS and ionic liquids in which films are produced by spin coating or by gelation and elimination of the solvent. In both cases the compositions are not suitable to be applied on fabrics through industrial or craft techniques such as screen printing, stencil or drawing with a brush to produce textile electrodes as it is not indicated how to control the viscosity of the compositions. In fact, the spin coating application is not suitable for textile production as it requires the rotation of the product which must have sufficient rigidity. At the same time inks with low viscosities lead to very low print resolutions as the formulations are too liquid and are absorbed by the fabric, producing irregular, undefined shapes and consequently non-standardized electrodes. US2012/043530 teaches to obtain compositions in gel form which however is a physical form which irreparably compromises the obtainment of textile electrodes as defined in the present invention. US 2008/139710 and JP2006 257148A describe compositions based on a conductive polymer in which the ionic liquid is present as the solvent of said conductive polymer. These compositions are not suitable to be used as ink for the printing of electrodes, although they are also applied on fabrics, since the removal of the solvent cannot take place by evaporation. The fabric will be wet with the ionic liquid making it uncomfortable and greatly reducing its resistance to washing, even if an additional gelling agent is added to the composition over the entire volume of the composition.

WO0216007746 teaches how to prepare a gel that can be aqueous and from which the water can be removed to make it an electrode. The polymer composition thus treated cannot be used as ink because the electrodes obtained are too resistive and not suitable for acquiring signals such as ECG.

In the literature there are no studies concerning the applications of solutions based on PEDOT and ionic liquids for the preparation of compositions to be used as inks on fabrics, nor for the preparation of electrodes for the detection of bioelectric parameters, a field that therefore remains completely unexplored in as far as the compositions known to date are not usable for making electrodes applicable to printing on wearable fabrics and articles and/or do not solve the problems of resistance to washing of the clothes on which the electrodes are applied. Furthermore, electrodes consisting of a single polymeric layer and not covered with a protective membrane that can constantly detect bioelectric parameters of the human body both in wet or dry skin conditions and in alternating situations of dry skin are not available.

SUMMARY OF THE INVENTION

The object of the present invention is to provide a composition for a conductive polymeric material suitable for the production of electrodes for recording electrophysiological signals, from active and passive measurements, such as ECG and variation of the body or skin impedance.

Another purpose is the application of this polymeric material on fabrics and in general materials suitable to be worn. This conductive polymeric material/fabric combination has a low skin/electrode impedance of less than 1000 k$\Omega$, preferably less than 800 k$\Omega$, less than 600, less than 400, less than 300, less than 200, less than 150, less than 100$\Omega$, without the addition of gel or saline solution, and allows to overcome the drawbacks of the prior art.

For this purpose a formulation containing PEDOT and ionic liquids according to the general formula (I) explained below has been developed. Preferred is the PEDOT salified with anions chosen from: polystyrenesulphonate, perchlorate, tetrafluoroborate, hexafluorophosphate, nitrate, sulphate, chloride, tosylate, sulphonamides with fluorinated substituents such as bis-(trifluoromethyl)sulphonyl-amide, bis-(perfluoroethyl)sulphonyl-ammide, bis-(heptafluoropropinyl)-sulphonyl-amide and bis-(nonafluoro-butinyl)sulphonyl-amide and sulphonated with fluorinated substituents, such as triflate ion, nonafluorobuthane sulphonate and heptadecafluoroectane sulphonate. Particularly preferred is PEDOT:PSS.

Preferred Ionic Liquids are:

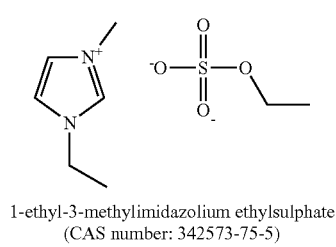

1-ethyl-3-methylimidazolium ethylsulphate
(CAS number: 342573-75-5)

(II)

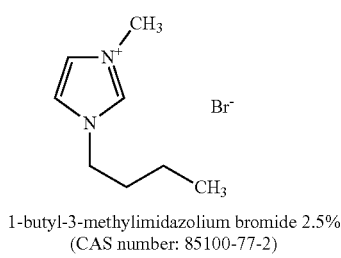

1-butyl-3-methylimidazolium bromide 2.5%
(CAS number: 85100-77-2)

(III)

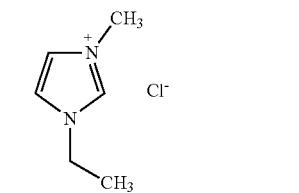

1-ethyl-3-methylimidazolium chloride
(CAS number: 65039-09-0)

(IV)

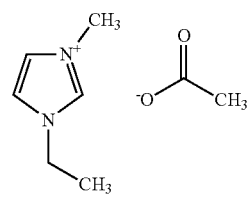

1-ethyl-3-methylimidazolium acetate
(CAS number: 143314-17-4)

(V)

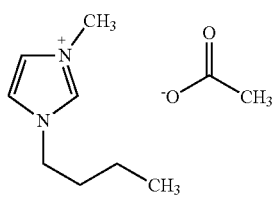

1-butyl-3-methylimidazolium acetate
(CAS number: 284049-75-8)

(VI)

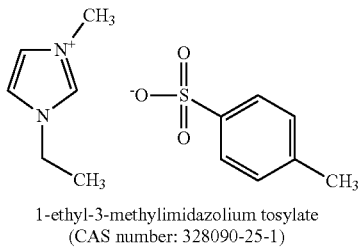

1-ethyl-3-methylimidazolium tosylate
(CAS number: 328090-25-1)

(VII)

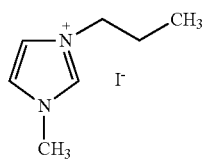

1-methyl-3-propylimidazolium iodide
(CAS number: 119171-18-5)

(VIII)

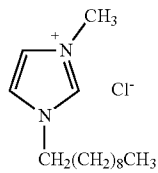

1-decyl-3-methylimidazolium chloride
(CAS number: 171058-18-7)

(IX)

Therefore a first object of the invention is to provide a conductive polymeric composition comprising the ionic liquids as defined above aimed at the preparation of textile electrodes, as defined below.

Another object of the invention is to provide electrodes for recording bioelectric signals using a conductive polymeric composition comprising the ionic liquids defined above. These electrodes are in fact made of polymeric material and therefore have mechanical properties compatible with the wearable fabric or article on which they are applicable, not being an obstacle to their lightness and comfort.

A further object of the invention is to provide electrodes for recording bioelectric signals to be applied directly on fabrics with conventional printing techniques, compatible with the manufacturing procedures typical of the textile industry, such that the articles thus obtained are resistant to washing by hand and in the washing machine.

Another object of the invention is to provide a method for preparing a conductive polymeric composition as defined above. The method comprises the following basic stages:
(i) Mixing of a commercial suspension of PEDOT, of any secondary dopant and of the ionic liquid, as specified below;
(ii) Thermal treatment of evaporation/thickening in order to obtain the appropriate chemical-physical properties for application on fabric;
(iii) Application on fabric of aliquots of the material obtained, through known techniques such as stencils, screen printing or other suitable known techniques;
(iv) drying in a stove to remove the solvent.

Aliquots of the material thus obtained can be used for the production of electrodes to be applied on fabrics for the detection of bioelectric parameters; for this purpose the electrodes can be connected with systems known per se to the reading electronics.

Another object of the invention is a device for detecting bioelectric parameters wherein the sensor comprises an electrode comprising the polymer composition of the invention based on PEDOT and an ionic liquid according to the formula (I) indicated below. The device according to the invention allows to detect electrophysiological signals from passive measurements, such as, by way of example and not limited to: electrocardiogram, electromyogram, electroencephalogram, electrooculogram, electrodermal activity, etc. or active such as, by way of example and not limited to: electrodermal activity, bioimpedance, etc.

Still another object are manufactured articles comprising electrodes made with the polymeric material of the invention, in particular wearable manufactured articles. These products are resistant to hand and machine washing.

Further objects will become apparent from the detailed description of the invention which follows.

BRIEF DESCRIPTION OF THE FIGURES

The invention will be better understood by referring to the detailed description when considered in combination with the non-limiting examples and the attached drawings, in which.

DETAILED DESCRIPTION OF THE INVENTION

Figure 1:
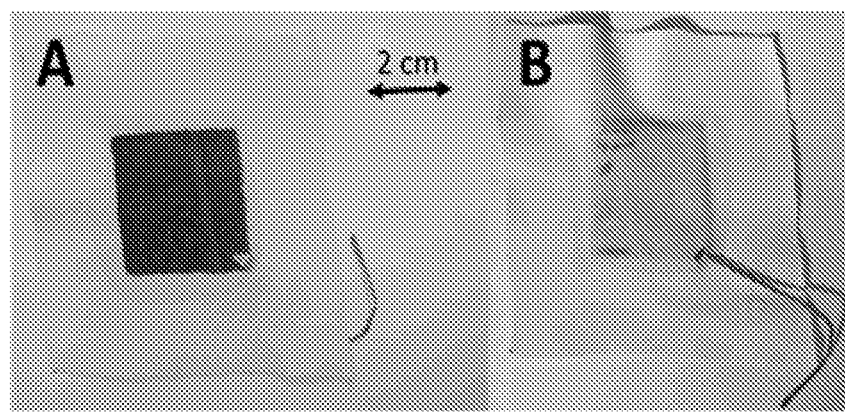
FIG. 1 shows a photograph of the electrode printed on bioceramic fabric (FIG. 1A) and of the back of the fabric on which the electrode was printed (FIG. 1B)
Figure 2:
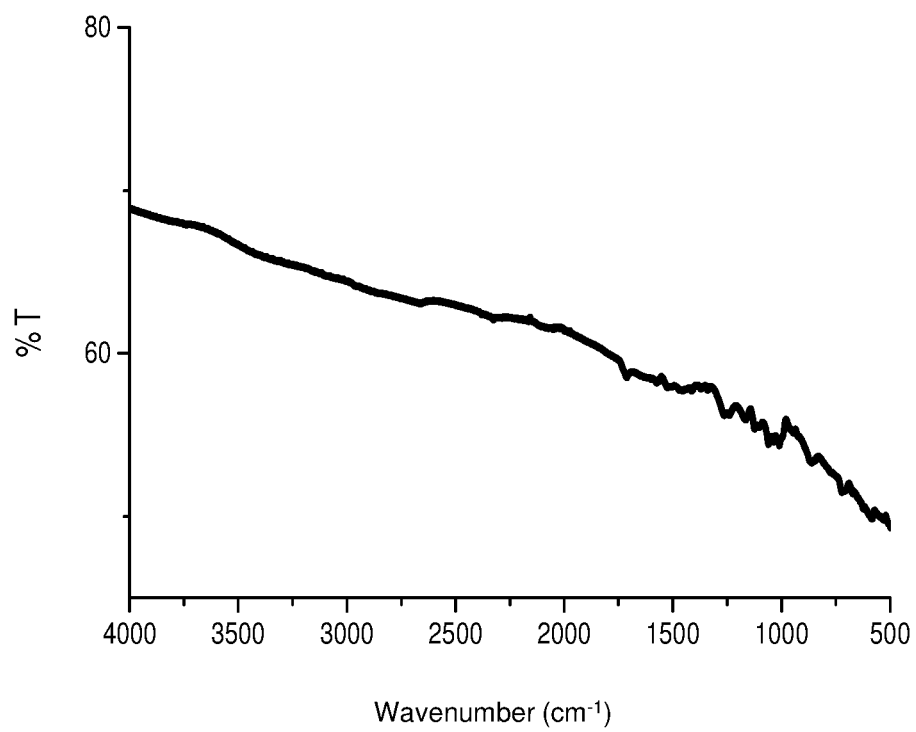
FIG. 2 shows the IR spectrum recorded on a PEDOT electrode: PSS with the addition of 1-ethyl-3-methylimidazolium printed on bioceramics.
Figure 3:
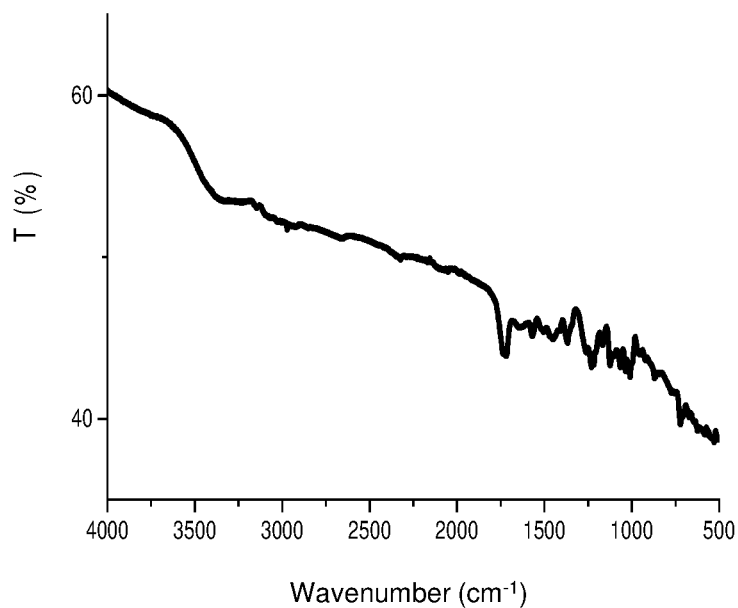
FIG. 3 shows the IR spectrum recorded on a PEDOT electrode: PSS with the addition of 1-ethyl-3-methylimidazolium chloride printed on bioceramics.
Figure 4:
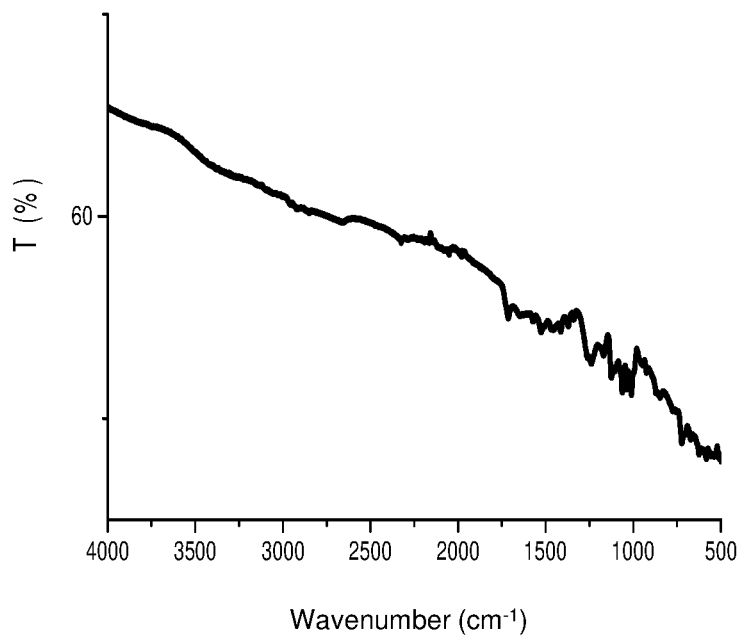
FIG. 4 shows the IR spectrum recorded on a PEDOT electrode: PSS with the addition of 1-butyl-3-methylimidazolium bromide printed on bioceramics.
Figure 5:
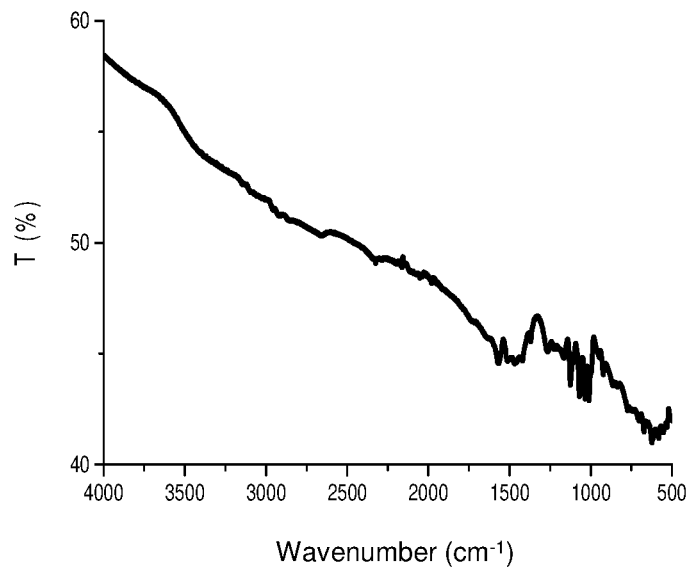
FIG. 5 shows the IR spectrum recorded on a PEDOT electrode: PSS with the addition of 1-butyl-3-methylimidazolium acetate printed on bioceramics.
Figure 6:
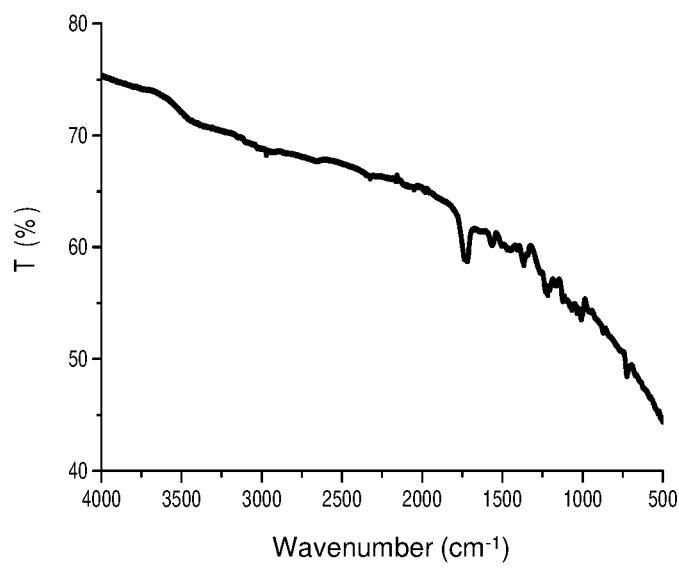
FIG. 6 shows the IR spectrum recorded on a PEDOT electrode: PSS with the addition of 1-ethyl-3-methylimidazolium acetate printed on bioceramics.
Figure 7:
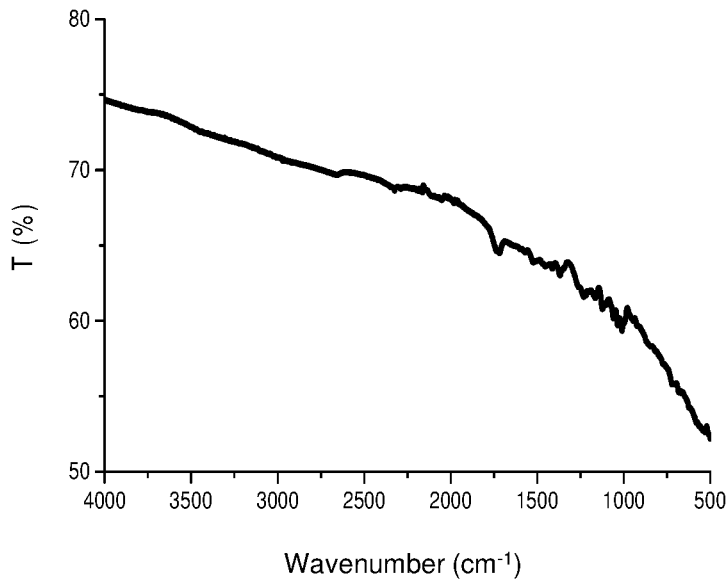
FIG. 7 shows the IR spectrum recorded on a PEDOT electrode: PSS with the addition of 1-ethyl-3-methylimidazolium tosylate printed on bioceramics.
Figure 8:
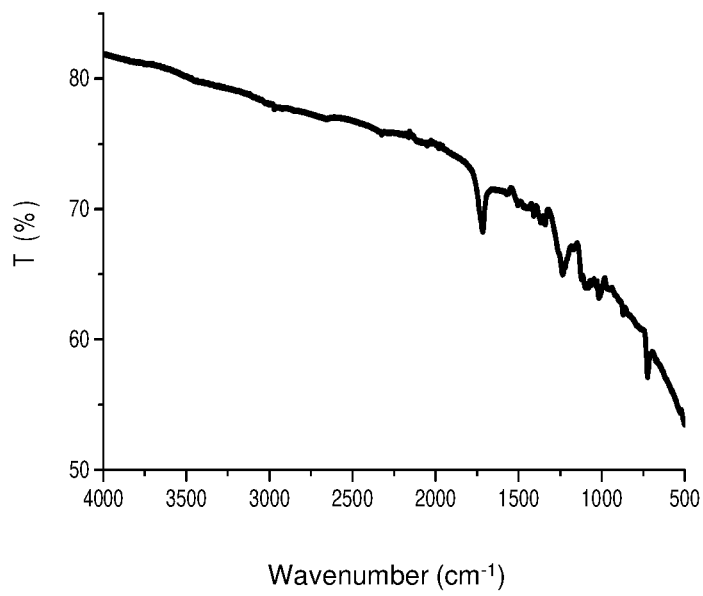
FIG. 8 shows the IR spectrum recorded on a PEDOT electrode: PSS with the addition of 1-methyl-3-propylimidazolium iodide printed on bioceramics.
Figure 9:
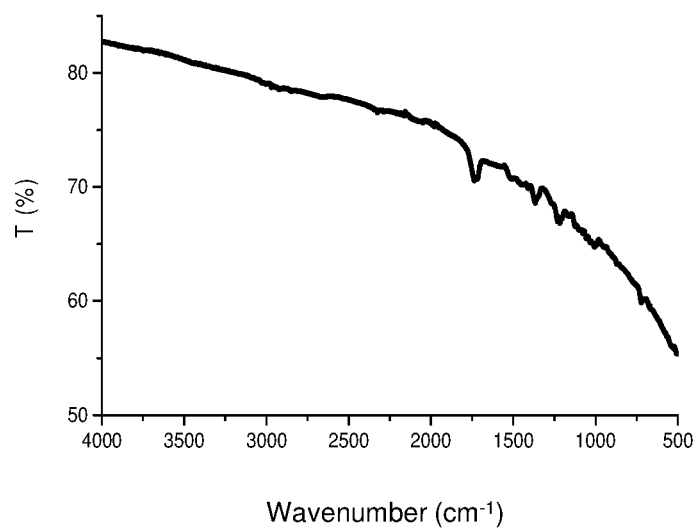
FIG. 9 shows the IR spectrum recorded on a PEDOT electrode: PSS with the addition of 1-decyl-3-methylimidazolium chloride iodide printed on bioceramics.

In the context of the present invention, the term "bioelectric signals" or "electrophysiological" refers to identify the electrical signals that can be continuously measured by living beings in the form of current voltages. The best known bioelectric signals are the electrocardiogram, electroencephalogram, electromyogram, electrodermal activity and electrooculogram. Other signals, linked to active measurements on the subject, or that involve the injection of an alternating current of very small entity for the measurement of the impedance of the body or skin, and of its variations, such as measures of respiratory frequency using impedance techniques, impedance tomography or active electrodermal response, can also be considered within the scope of the present invention.

The invention allows to detect bioelectric signals through polymeric electrodes printed on fabric. For example, the new formulation of the PEDOT, preferably PEDOT:PSS, described here, allows the acquisition of the signal without hydration or the use of gel or other additional layers of materials.

The conductive composition according to the invention includes: the combination poly-(3,4-ethylenedioxytophene): anion, also simply called PEDOT, preferably the poly-(3,4-ethylenedioxytophene) combination: poly-(styrene-sulphonate) (called hereinafter PEDOT:PSS), and at least one ionic liquid of general formula (I):

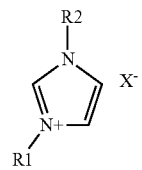

wherein
R1 and R2 independently of each other are branched or cyclic linear alkyl groups, with chain $C_1$-$C_{15}$, preferably $C_1$-$C_{10}$
X is an anion selected from alkylsulphates, tosylate, carboxylates $C_1$-$C_5$, such as for example formate and acetate, halides such as fluorides, chlorides, fluorides, bromides and iodides, borates and phosphates, such as tetrafluoro borate and hexafluorophosphate, sulphonates taken individually or in a mixture.

The following compounds are preferred:
1-ethyl-3-methylimidazolium ethylsulphate (CAS: 342573-75-5)
1-ethyl-3-methylimidazolium chloride (CAS number: 65039-09-0)
1-butyl-3-methylimidazolium bromide (CAS number: 85100-77-2)
1-butyl-3-methylimidazolium acetate (CAS number: 284049-75-8)
1-ethyl-3-methylimidazolium acetate (CAS number: 143314-17-4)
1-ethyl-3-methylimidazolium tosylate (CAS number: 328090-25-1)
1-methyl-3-propylimidazolium iodide (CAS number: 119171-18-5)
1-decyl-3-methylimidazolium chloride (CAS number: 171058-18-7).

A compound with the function of secondary dopant can be added to the PEDOT/ionic liquid combination, chosen from ethylene glycol, dimethylsulphoxide, dimethylformamide, methoxyethanol, diethylene glycol, dimethyl sulphate, xylitol, glycerol, sorbitol and meso-erythritol. These substances increase the crystallinity of the PEDOT, have the function of increasing the conductivity of the final composition and are widely known in the literature.

The ratios of the individual components of the composition are in the following percentages by weight with respect to the final mass of the solution:

Conductive polymer suspension (PEDOT) 49.9-99.9% (PEDOT concentration between 1-10%), therefore the composition of the invention has a conductive polymer concentration of 0.2-10%, secondary dopant 0-50%, ionic liquid 0.05-2.0%. Preferred is 1-butyl-3-methylimidazolium acetate, which is added in an amount of 0.1-2.0%; and the ratio (conductive polymer)/(ionic liquid) is comprised between 0.5 and 15, preferably between 0.66 and 2.

The above mentioned composition is suitable above all with the use of PEDOT:PSS.

In this case, cross-linkers known per se as GOPS (can be added 3-glycidoxypropyl-trimethoxysilane), typically in an amount of 0.05-1.5% by weight, with the aim of creating a bond between the various PEDOT:PSS particles in the suspension and subsequently in the polymer film. Furthermore, surfactants, such as for example dodecyl benzene sulphonic acid, can be added to decrease the surface tension between ink and substrate in order to improve the coating of the substrate by the ink.

The compositions thus identified have the appearance and characteristics of an ink, are in fact blue in color, and are applied as described below on textile supports and/or materials for wearable clothing in order to be used as electrodes for bioelectric measurements.

Ionic liquids have an unexpected thickening effect, since a slight heating (between 1 and 60 minutes in an oven at a temperature between 50 and 70° C.) is sufficient at the concentration of 1% to lead to the formation of a liquid with the right viscosity (between 100 and 10000 cP) for the applications according to the invention, in particular in the processes of screen printing, stencil or brush.

The conductive compositions thus identified, also called inks below, are viscous but not gelled compositions. It should be remembered that the gel is characterized by a solid matrix in which a liquid phase is dispersed, and therefore has its own shape, unlike the compositions of the invention which, although very viscous, are not gels. In fact, the compositions of the invention are used before reaching gelation, which is intended as an irreversible condition in which the ink takes on its own shape characterized by a solid structure in which a liquid phase is incorporated and involves a worsening of the electrical characteristics of the molded electrodes. Within the scope of the present invention, the term "textile electrode" means an electrode prepared by applying the conductive composition of the invention directly onto a textile support capable of being placed in direct contact with the skin. The combination of conductive composition and support will be suitable to ensure the maintenance of the mechanical/sensorial characteristics of the fabric itself, such as flexibility, density in weight, comfort and fit, while maintaining the electrical characteristics unchanged even after washing in water or in the washing machine. The composition object of the invention allows to prepare this type of electrode by applying it with a brush or with printing techniques, such as for example the stencil or the screen printing. The viscosity of the ink is such as to allow to obtain a shape with defined contours on a support, such as a fabric, which can be used to create wearable articles. Within the scope of the present invention, therefore, application methods are excluded which provide for the manufacture of low viscosity inks, such as the spin coating technique, which in fact do not adapt to the application on textile supports, as they do not produce regular and standardized shapes.

As indicated above, the compositions according to the invention are aqueous suspensions which comprise (% by weight):

conductive polymer (PEDOT) in an amount between 0.2 and 10% (generally obtained from commercial suspensions in which the concentration of conductive polymer is 49.9-99.9%), ionic liquid 0.05-2.0% (preferred is 1-butyl-3-methylimidazolium acetate, which is added in an amount of 0.1-2.0%), secondary dopant 0-50%, ratio (ionic liquid)/(conductive polymer) between 0.5 and 15, preferably between 0.66 and 2, water 30-99% by weight and, once the mixture of the individual components is prepared, to obtain the textile electrodes according to the invention, the water is evaporated in two stages, the first being carried out until obtaining a viscosity of the mixture between 100 and 10000 cP measured under standard conditions, the second for the almost complete elimination of water. Between the first and second evaporation stages, the application will be carried out on the substrate.

These operating modes allow to obtain a constancy of characteristics, in terms of recorded bioelectric signals, which remains unchanged even after several washes of the wearable articles on which the textile electrodes are applied.

Not to mention that the process is particularly interesting from an industrial point of view as it is simple to carry out and allows at the same time to obtain easily standardized wearable articles.

A method for obtaining the formulation according to the invention comprises the following basic stages:

(i) Mixing of the commercial suspension of the conductive polymer (PEDOT), of the secondary dopant and of the ionic liquid. The mixing can be carried out in the laboratory first manually with the aid of a glass rod and then placing the mixture thus prepared in an ultrasonic bath. It is preferable that the mixing is carried out immediately after the addition of the ionic liquid to the suspension of PEDOT due to the thickening effect of the additive.

(ii) It is preferable that the use of the suspension indicated above is carried out within 3-4 hours from the mixing of the components, otherwise gelation phenomena occur, due to the presence of the ionic liquid, which risk leading to poor performance of the final composition. The gelation is evidenced by a phase separation in which in a first phase the conductive polymer is present together with the ionic liquid and in the second phase the water solvent is present. Once gelled, or having a continuous solid structure in which a liquid phase is incorporated, the composition cannot be returned to the initial fluid state and its characteristics are irreparably compromised, also compromising its subsequent formulation as ink to make the electrodes of the invention, since its electrical conductivity is at least one order of magnitude lower. Possible heat treatment of evaporation of the solvent and consequent thickening in order to obtain the appropriate chemical-physical properties for application on fabric, indicated by a viscosity of the mixture, which has the appearance of a viscous ink, between 100 and 10000 cP measured under standard conditions. The viscosity was measured with HAAKE ROTOVISCO 1 VISCOSIMETER. The heat treatment to obtain the aforementioned viscosity can be carried out in the air or by drying in an oven between 0 and 60 minutes at a temperature between 40 and 100° C., preferably 50-70° C. The viscosity indicated above is considered optimal for the subsequent steps of the application on the substrate.

(iii) Application on a substrate suitable to be placed in contact with the epidermis of an aliquot of the composition obtained in step (ii) (as a non-limiting example, about 0.5 g is used for printing a 2 cm×2 cm square) through known printing techniques such as, for example, not limiting: stencil or brush, screen printing or other suitable techniques known per se.

(iv) Stove drying of the products obtained in the previous stage (iii) for the elimination of the solvent (20°-150° C. for a time greater than 5 min) which usually consists of water and a possible secondary dopant added to the suspension of PEDOT. The electrode thus obtained and the surrounding fabric will be permanently impregnated with the ink mixture containing the conductive polymer and the ionic liquid which, due to the low vapor pressure, cannot evaporate.

At this stage of the preparation an electrode made of conductive polymeric material was obtained. We then move on to the next stage which is:

(v) Manufacture of the contacts for the connection with the reading electronics. The ideal contacts are made with a conductive material wire and using a conductive glue (for example silver) to facilitate the charge transfer between the wire and the electrode.

A non-limiting list of suitable substrates to be placed in contact with the epidermis is as follows: fabric, elastic fabric, non-woven fabric, rubbers, polyurethane foams, fibers, plastic films, relative combinations and all the materials that can generally be used to make wearable products. The fabrics can be all conventional fabrics and technical fabrics made with natural, vegetable, synthetic fibers and their blends.

The strong point of the invention is the formulation of the preparation to be applied to the substrate which allows to obtain PEDOT electrodes for the recording of bioelectric signals without the use of gels or moisturizing solutions.

The formulation according to the invention can be used generically in the context of detecting bioelectric signals and can be applied on wearable articles, in particular in fabric, such as, for example, a shirt, so as to be in direct contact with the areas of the body subject to detection. The products on which to apply the formulation can be flexible and wearable products, including diving articles, such as watertight suits, and for water sports and underwater surveys, in particular articles used in the medical and health sector such as plasters, elastic support bands and adhesive support bands and textile products, including those made of special fabrics such as bioceramics.

Ionic liquids are used as thickeners for the production of the compositions of the invention.

The manufactured items are washable and it has been verified that after 20 washes they still maintained good electrical response characteristics.

The compositions are suitable to be applied directly on the skin and the tests carried out have not detected skin irritation.

The compositions of the invention are suitable for being used in printing techniques as an ink would be used. They are applied when a certain amount of solvent (water+ possibly secondary dopant) is still present which gives the appropriate viscosity for printing applications. The optimal quantity of solvent depends on the ionic liquid used and is between 40 and 99%. The application of the composition can be carried out until no phase separation has yet taken place or the material has acquired a well-defined proper shape, which differentiates it from a proper fluid. This condition occurs when a thick, viscous but not gelled viscous liquid is obtained. Depending on the printing applications, the viscosities can vary from 100 to 10000 cP measured under standard conditions.

In fact, the formulations described are suitable to be applied with printing techniques because they have an optimal final ratio between ionic liquid and conductive polymer between 0.05 and 2, preferably between 0.5 and 1.5. This ratio allows for constant electrical characteristics over time, combined with excellent resistance to washing, as well as allowing the electrical responses to be kept constant even with a great alternation of dry/wet skin cycles, typical of athletes.

In conclusion, the compositions to be used as inks on fabrics, and the electrodes for the detection of bioelectric parameters thus obtained, solve the problems of resistance to washing of the clothes on which the electrodes are applied and allow the bioelectrical parameters to be detected with constant results of a human body both in conditions of wet and dry skin and in alternating situations of dry/wet skin. A further advantage of the invention results from the ease of industrial implementation and relative standardization of the manufactured articles obtained.

The following examples are illustrative of the invention and are in no case to be considered limitative of the relative scope.

EXAMPLES

An example of construction of the electrodes involves mixing the reagents with the following procedure.

The suspension of PEDOT:PSS PH 1000 in water (suspension purchased from Heraeus) is stirred in an ultrasonic bath (Bandelin Sonorex Super RK 510, power=2×320 W) for 10 min. The suspension of PEDOT:PSS, the secondary dopant and the ionic liquid are mixed in the proportions shown in table 1, taking care to maintain a good stirring, using a glass rod. The suspension obtained is placed in an ultrasonic bath for 10 min.

The composition is placed in a petri dish in order to have a liquid with a height of a few mm. The plate is placed in an oven at 70° C. until the material turns out to be a very viscous liquid (viscosity between 100 and 10000 cP). The preparation thus obtained was used to obtain textile electrodes in various embodiments.

TABLE 1

Composition of the various preparations object of the invention

| mass$_{PEDOT:PSS}$(g) | Secondary | Mass$_{secondary\ dopant}$(g) | Ionic | Mass$_{ionic\ liquid}$(g) |
|---|---|---|---|---|
| 8.90 | Ethylene glycol (Merck) | 1.00 | 1-ethyl-3-methylimidazolium ethylsulphate (Sigma-Aldrich) | 0.10 |
| 8.90 | Dimethylsulphoxide (Sigma-Aldrich) | 1.00 | 1-ethyl-3-methylimidazolium ethylsulphate | 0.10 |
| 8.75 | Dimethylsulphoxide | 1.00 | 1-ethyl-3-methylimidazolium chloride (Sigma-Aldrich) | 0.25 |
| 8.75 | Dimethylsulphoxide | 1.00 | 1-butyl-3-methylimidazolium bromide (Sigma-Aldrich) | 0.25 |
| 8.90 | Dimethylsulphoxide | 1.00 | 1-butyl-3-methylimidazolium acetate (Sigma-Aldrich) | 0.10 |
| 8.90 | Dimethylsulphoxide | 1.00 | 1-ethyl-3-methylimidazolium acetate | 0.10 |
| 8.90 | Dimethylsulphoxide | 1.00 | 1-ethyl-3-methylimidazolium tosylate (Sigma-Aldrich) | 0.10 |
| 8.90 | Dimethylsulphoxide | 1.00 | 1-methyl-3-propylimidazolium iodide (Sigma-Aldrich) | 0.10 |
| 8.98 | Dimethylsulphoxide | 1.00 | 1-decyl-3-methylimidazolium chloride (Sigma-Aldrich) | 0.02 |

Embodiment 1: Electrodes on Single Pieces of Fabrics Printed with Stencil

The electrode is made on bioceramic fabric with two stencil printing steps using a square mask with a side of 2 cm.

An aliquot of about 0.5 g of the viscous liquid prepared previously is used. The preparation is placed on one side of the square which identifies the printing area, and with the help of a spatula the composition is dragged onto the mask so as to make it come into contact with the fabric. In the printing area the fabric appears impregnated with ink with a strong blue color. The fabric is placed in an oven at 60° C. for about 15 minutes. A second printing step is subsequently carried out so that a greater quantity of preparation remains on the fabric. A professionally conducted print should not present lumps of PEDOT:PSS.

The electrode is dried in a stove for 30 min until the solvent consisting of water and secondary dopant has completely evaporated. FIG. 1 shows the photo of the electrode, using 1-ethyl-3-methylimidazolium ethylsulphate as an ionic liquid and as a secondary dopant dimethylsulphoxide, printed on fabric. The electrode and the surrounding fabric still appear impregnated with the ionic liquid which, due to the low vapor pressure, cannot evaporate.

Figure 10:
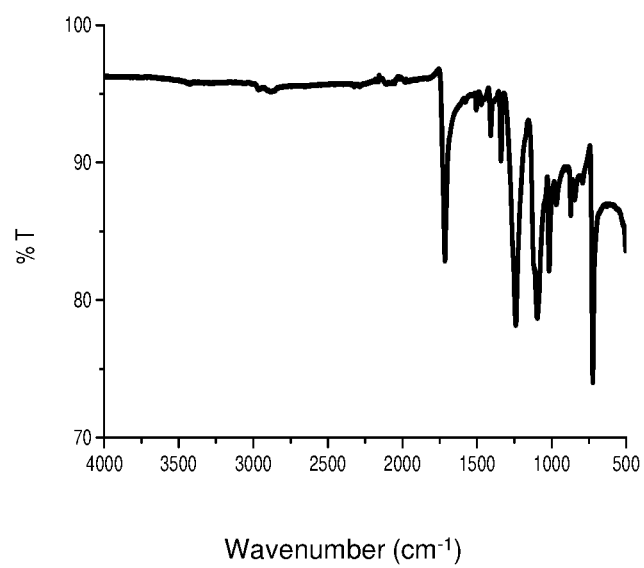
FIG. 10 shows the IR spectrum recorded on a PEDOT electrode: PSS printed on bioceramics.
Figure 11:
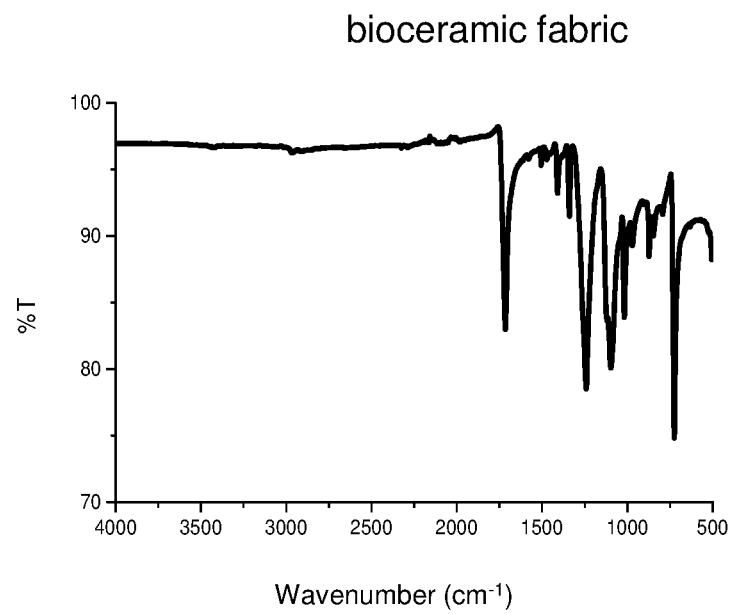
FIG. 11 shows the IR spectrum recorded on bioceramic fabric.

The collectors for signal extraction are made by sewing a metal wire near a vertex of the square based on PEDOT which constitutes the electrode. The wire comes out from the back of the electrode as shown in FIG. 1B. An Ag-based conductive paint is placed in the interface between the metal wire and the PEDOT-based composition, in order to reduce the electrical contact resistances. The areas covered with Ag are then isolated with the aid of a silicone (polydimethylsiloxane, PDMS). The presence of the ionic liquid inside the conductive material is confirmed by the IR spectra (FIGS. 2-9) recorded on a bioceramic fabric for the various electrodes obtained. In addition, the IR spectra of the bioceramic fabric and of electrodes obtained with PEDOT:PSS only are shown in FIGS. 10 and 11. In the IR spectra of the PEDOT:PSS electrodes with ionic liquids, bands are observed at about 1577, 1164, 1057 and 622 cm$^{-1}$ not present in the IR spectra of the fabric and the electrode in PEDOT:PSS printed on bioceramics. These bands are related to the IR vibrations of the imidazole ring. In particular, the 622 cm$^{-1}$ band can be attributed to the stretching of the group $CH_3$(N)CN, while the 1164, 1057 and 1577 cm$^-$ bands are attributable to the stretching of the imidazole ring. These data demonstrate the presence in each electrode of the imidazole ionic liquids used as additives.

ECG Test (1)

Figure 12:
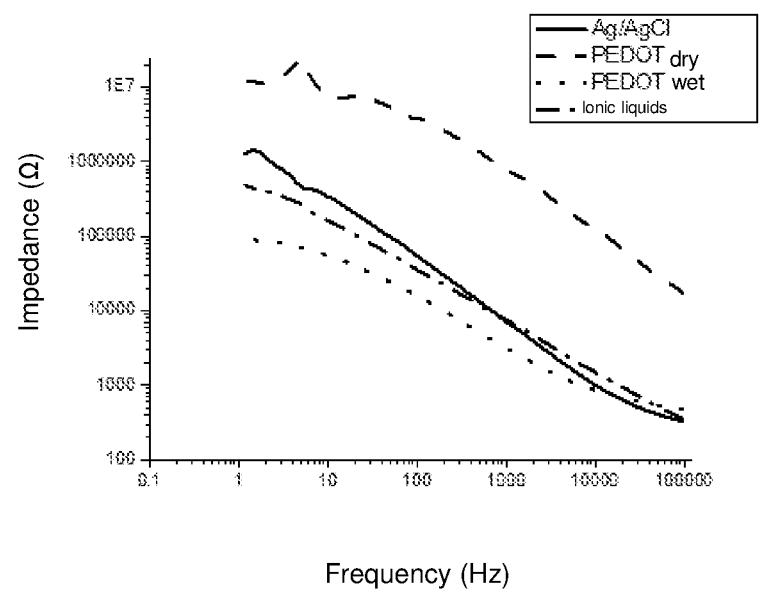
FIG. 12 shows the impedance spectrum recorded for commercial Ag/AgCl electrodes, dry and wet PEDOT:PSS base electrodes (without new additives) and PEDOT:PSS electrodes obtained using 1-ethyl-3-methylimidazolium ethylsulphate as an additive, object of the invention.
Figure 13:
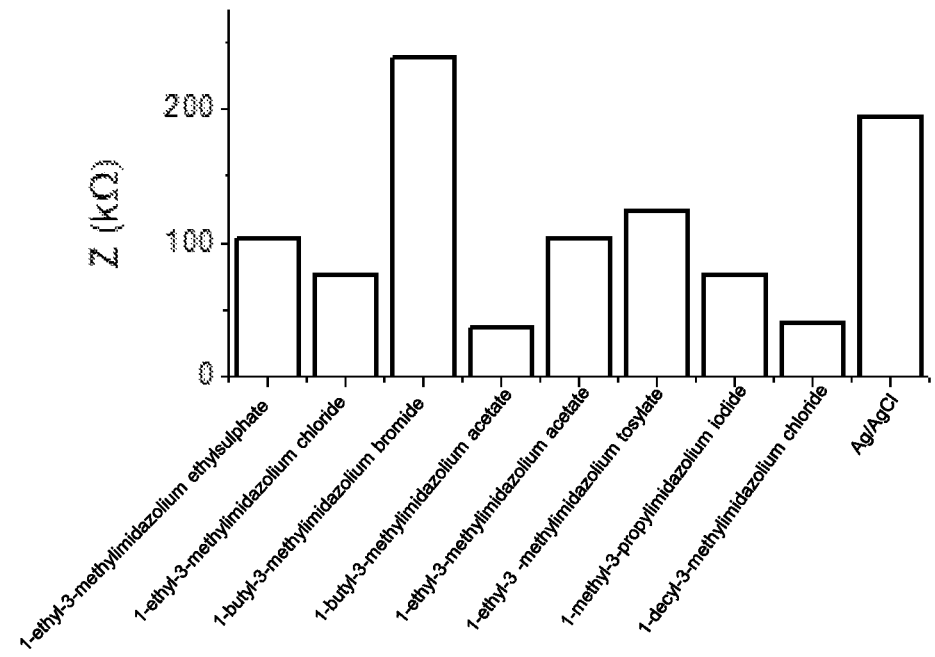
FIG. 13 shows the impedances recorded at 20 Hz for the electrodes of PEDOT:PSS printed on fabric and added with the various ionic liquids object of the invention.
Figure 14:
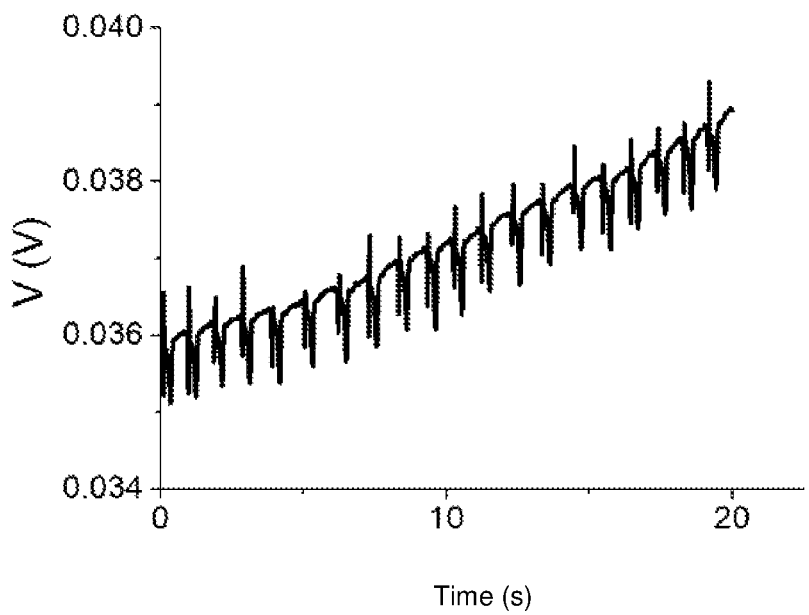
FIG. 14 shows the ECG tracing recorded with a pair of PEDOT:PSS electrodes obtained using 1-ethyl-3-methylimidazole ethylsulphate as additive.
Figure 15:
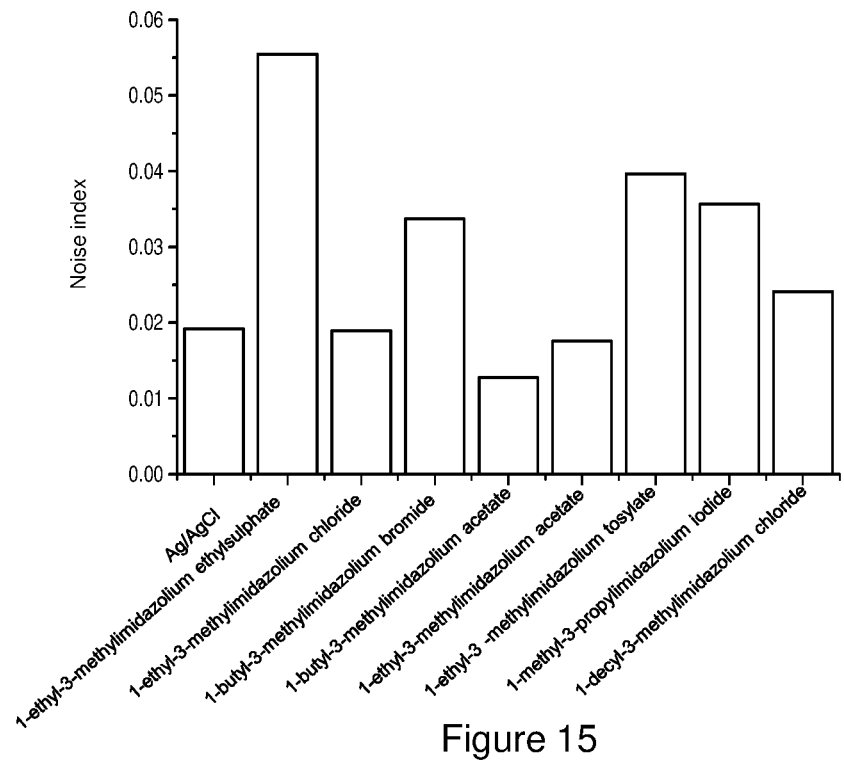
FIG. 15 shows the noise index values for the PEDOT electrodes: PSS printed on fabric and added with the various ionic liquids object of the invention.

The electrodes were used to acquire the ECG tracing of healthy volunteers. In particular, two textile electrodes were placed on the chest, with the skin dry and untreated, at a distance of about 10 cm, at the height of the xiphoid process, and an elastic band was used to maintain physical contact between the skin and electrode. The metal collectors have been connected to bench reading electronics (CH Instrument 660) to record both the impedance spectrum and the difference in electrical potential between the two electrodes. The impedance spectrum was recorded for commercial pre-gelled Ag/AgCl based ECG electrodes, PEDOT:PSS textile electrodes without the addition of ionic liquids and textile electrodes obtained with PEDOT:PSS added with 1-ethyl-3-methylimidazole ethylsulphate (FIG. 12). FIG. 12 clearly shows that the skin/electrode impedance obtained for the textile electrodes object of the present invention is significantly lower than that obtained with PEDOT:PSS textile electrodes produced according to the current state of the art. Furthermore, the impedance values for the textile electrodes of PEDOT:PSS with the addition of 1-ethyl-3-methylimidazole ethylsulphate are very similar to those of the pre-gelled commercial electrodes studied. Impedance spectra were recorded for all electrodes produced. FIG. 13 shows the impedance values recorded at 20 Hz for the PEDOT:PSS electrodes added with the various ionic liquids object of the invention and a pre-gelled Ag/AgCl electrode used as a comparison (Euro ECG Electrodes, FIAB, Vicchio Firenze). The 20 Hz value was chosen because it is close to the frequency used for acquiring ECG signals. The electrode prepared with 1-butyl-3-methylimidazolium bromide additive shows an impedance greater than 200 k$\Omega$, which however is adequate for the acquisition of the ECG signal. FIG. 14 shows the ECG trace obtained with the electrode object of the invention in which the PEDOT:PSS was added with 1-ethyl-3-methylimidazole ethylsulphate. At the same time the tests carried out with electrodes prepared with PEDOT:PSS only did not show an response. ECG traces were recorded for each electrode object of the invention, and the noise index was calculated in accordance with the literature (Computers in Cardiology 2007; 34: 157-160). All the electrodes show a noise index lower than 0.1 highlighting a good signal quality and underlining how it is possible to use them to acquire ECG signals.

ECG Test (2)

Figure 16:
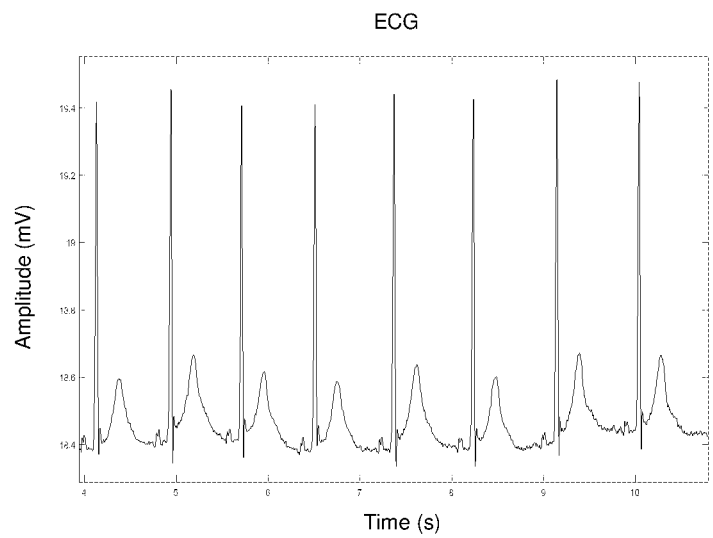
FIG. 16 shows the ECG of a male subject during mild physical activity.
Figure 17:
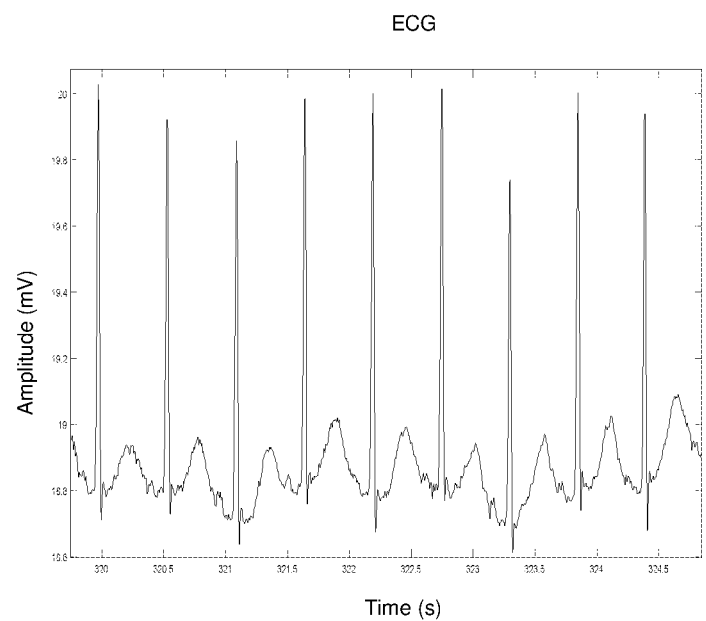
FIG. 17 shows the ECG of the same male subject of FIG. 16, during intense physical activity.
Figure 18:
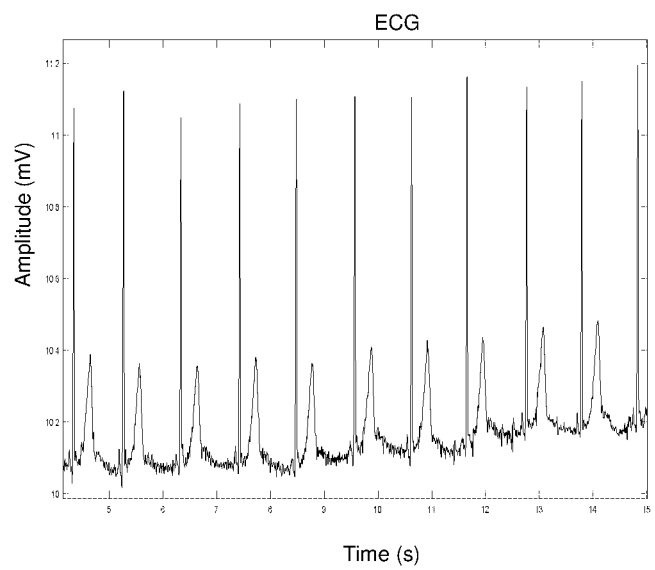
FIG. 18 shows the ECG of a female subject during mild physical activity.
Figure 19:
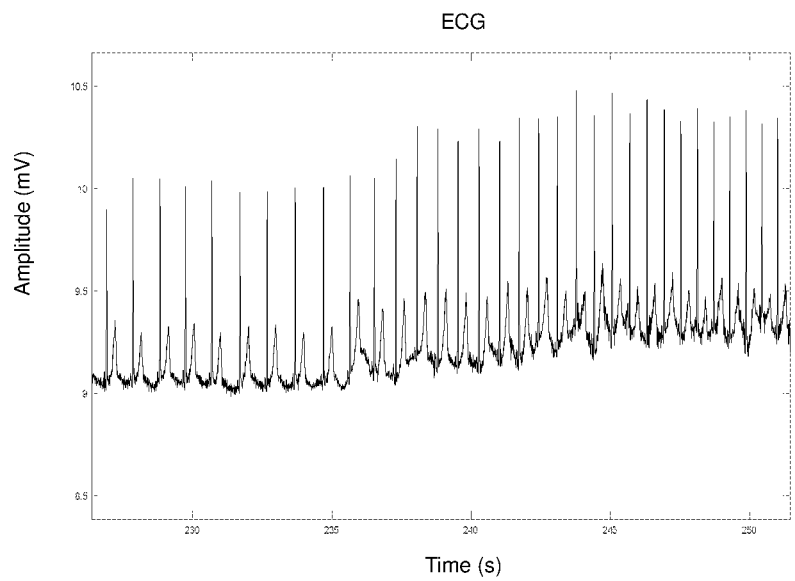
FIG. 19 shows the ECG of the same female subject, in the transition from moderate to intense physical activity.

A further test was carried out by directly printing the electrode on an adherent bioceramic mesh with an integrated compression band, positioning the electrodes in the same position as in the previous case, dry and in the absence of any preliminary skin treatment. Tests were performed on healthy volunteers in the presence of major (man) or minor (woman) compression of the electrode on the skin. The acquisition was carried out with a custom reading electronics based on the front-end for ECG and ADS1292R breath by Texas Instruments, with Bluetooth wireless transmission of the signal to a receiving device, in the absence of any analog or digital filter applied to the signal (raw data). Examples of signals acquired in different operating conditions are reported, so as to encourage the appearance of artifacts:

1. FIG. 16: male subject, mild physical activity
2. FIG. 17: male subject, intense physical activity
3. FIG. 18: female subject, mild physical activity
4. FIG. 19: female subject, transition to intense physical activity.

In all cases there is a perfectly clean signal, despite the absence of any form of filtering (note the presence of normal low frequency and high frequency artifacts, which otherwise would not be present).

Washability Tests

Washing Protocol

All the tests were carried out following a washing protocol similar to that of the reference standard ISO 105 C10: 2006. The fabric samples with the electrodes printed following the procedures indicated above are immersed in a 2.5 L beaker containing tap water and 20 grams of liquid detergent (Marseille for hand washing) at a temperature of about 40° C. They are subjected to a gentle stirring and a constant temperature for 30 minutes. Afterwards, the rinsing process takes place: water is poured with detergent and the beaker is filled with tap water at room temperature and stirred for 2 minutes. The electrodes are extracted and dried first with paper to remove excess water, then in an oven set at 60° C. for 35-40 minutes. This concludes a wash cycle.

Washing Test Example 1

A pair of electrodes was made on bioceramic fabric in the embodiment 1 described above, using 1-butyl methyl imidazolium acetate as the ionic liquid with the composition obtained as described in table 1. The pair of electrodes was characterized in terms of resistance, skin-electrode impedance and noise index in the electrocardiogram recording obtaining the following values 70·$\Omega$, 3.7·$10^4 \Omega$ and 0.013, respectively. The electrodes were subjected to 20 washing cycles and the resistance, electrode skin impedance and noise index in the recording of the electrocardiogram were measured every 5 washing cycles, showing good functioning up to the twentieth cycle. At the twentieth cycle the resistance was 2.4·$10^2 \Omega$ and the skin electrode impedance was 3.4·$10^5 \Omega$. The noise index was 0.068, still sufficient to record a good ECG.

Washing Test Example 2

A pair of electrodes was made on bioceramic fabric in the embodiment 1 using 1-ethyl-3-methylimidazolium acetate as the ionic liquid with the composition obtained as described in table 1. The pair of electrodes was characterized in terms of resistance, skin electrode impedance and noise index in the recording of the electrocardiogram obtaining the following values 1.3·$10^2 \Omega$, 1.0·$10^5 \Omega$ and 0.0176, respectively. The electrodes were subjected to 20 washing cycles and the resistance, electrode skin impedance and noise index in the recording of the electrocardiogram were measured every 5 washing cycles, showing good functioning up to the twentieth cycle. At the twentieth cycle the resistance was 1.7·$10^2 \Omega$ and the electrode skin impedance was 1.5·$10^6 \Omega$. The noise index was 0.038, still sufficient to record a good ECG.

Washing Test Example 3

Different pairs of electrodes were made in the embodiment 1 using 1-butyl methyl imidazolium acetate as the ionic liquid with the composition obtained as described in table 1. The electrodes were deposited on PRO 29518, OPY 170, THINK 27749, STRATEGY RAW CUT, PRO 29374 and THINK OPACITY. The electrodes were subjected to 15 washing cycles and the ability to read the ECG signal was verified every 5 washing cycles. The electrodes obtained on each type of fabric maintained the ability to record the ECG signal for 15 washing cycles.

TABLE 2

| | Initial values | | |
|---|---|---|---|
| Fabric | Resistance (k$\Omega$) | Impedance $\Omega$ (20 Hz) | Noise index (tot) |
| PRO 29518 | 0.16 | $3.70 \cdot 10^6$ | 0.069108 |
| OPY 170 | 0.18 | $5.18 \cdot 10^5$ | 0.026673 |
| THINK 27749 | 0.084 | $2.43 \cdot 10^5$ | 0.019501 |
| STRATEGY RAW CUT | 0.3 | $9.28 \cdot 10^4$ | 0.025904 |
| PRO 29374 | 0.1 | $1.75 \cdot 10^5$ | 0.016133 |
| THINK OPACITY | 0.08 | $1.21 \cdot 10^5$ | 0.01351 |
| | Values after 15 washing cycles | | |
| Fabric | Resistance (k$\Omega$) | Impedance $\Omega$ (20 Hz) | NI m (tot) |
| PRO 29518 | 0.22 | $1.71 \cdot 10^5$ | 0.03207 |
| OPY 170 | 0.89 | $3.99 \cdot 10^4$ | 0.02112 |
| THINK 27749 | 0.37 | $3.70 \cdot 10^4$ | 0.01627 |
| STRATEGY RAW CUT | 0.69 | $1.04 \cdot 10^5$ | 0.02915 |
| PRO 29374 | 0.294 | $9.42 \cdot 10^4$ | 0.02074 |
| THINK OPACITY | 0.47 | $1.69 \cdot 10^5$ | 0.01524 |

Washing Test Example 4

A pair of electrodes was made on bioceramic fabric in the embodiment 1 using 1-butyl methyl imidazolium acetate as an ionic liquid with a obtained composition to which a crosslinker was added. The composition was prepared by starting by mixing 8.4 g of suspension of PEDOT:PSS PH 1000, 1.0 g of dimethyl sulphoxide, 0.10 g of 1-butyl methyl imidazolium and 0.5 g of 3-(glycidyloxypropyl) trimethoxysilane. The electrodes were subjected to 25 washing cycles and the ability to read the ECG signal was verified every 5 washing cycles. At the twenty-fifth cycle the resistance was $1.0 \cdot 10^3 \Omega$ and the skin electrode impedance was $3.9 \cdot 10^4 \Omega$. The noise index was 0.024, still sufficient to record a good ECG.

Breath Test

Figure 20:
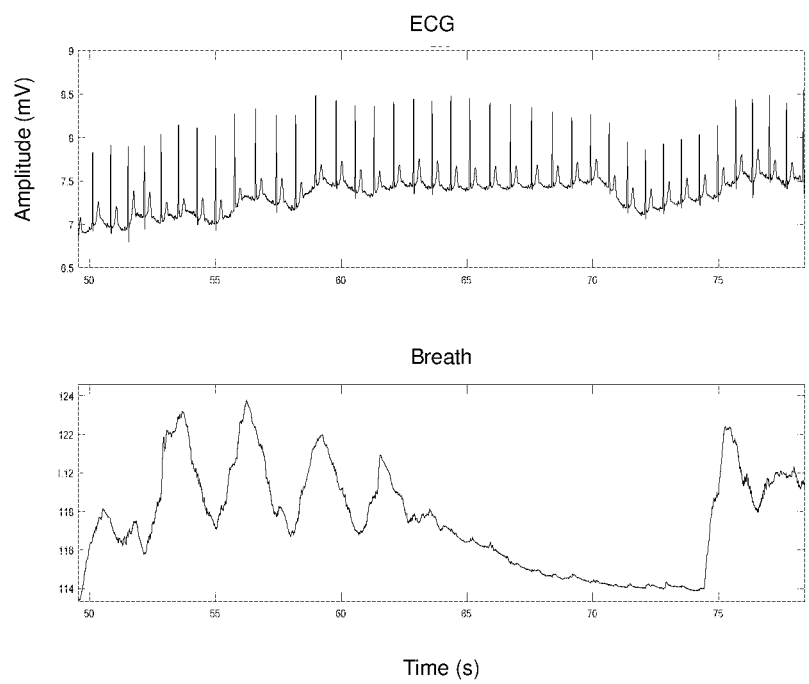
FIG. 20 shows the traces of ECG and BREATH (acquired with impedance technique from the same electrodes used for ECG, simultaneously) acquired on a subject that alternates normal breathing with apnea.
Figure 21:
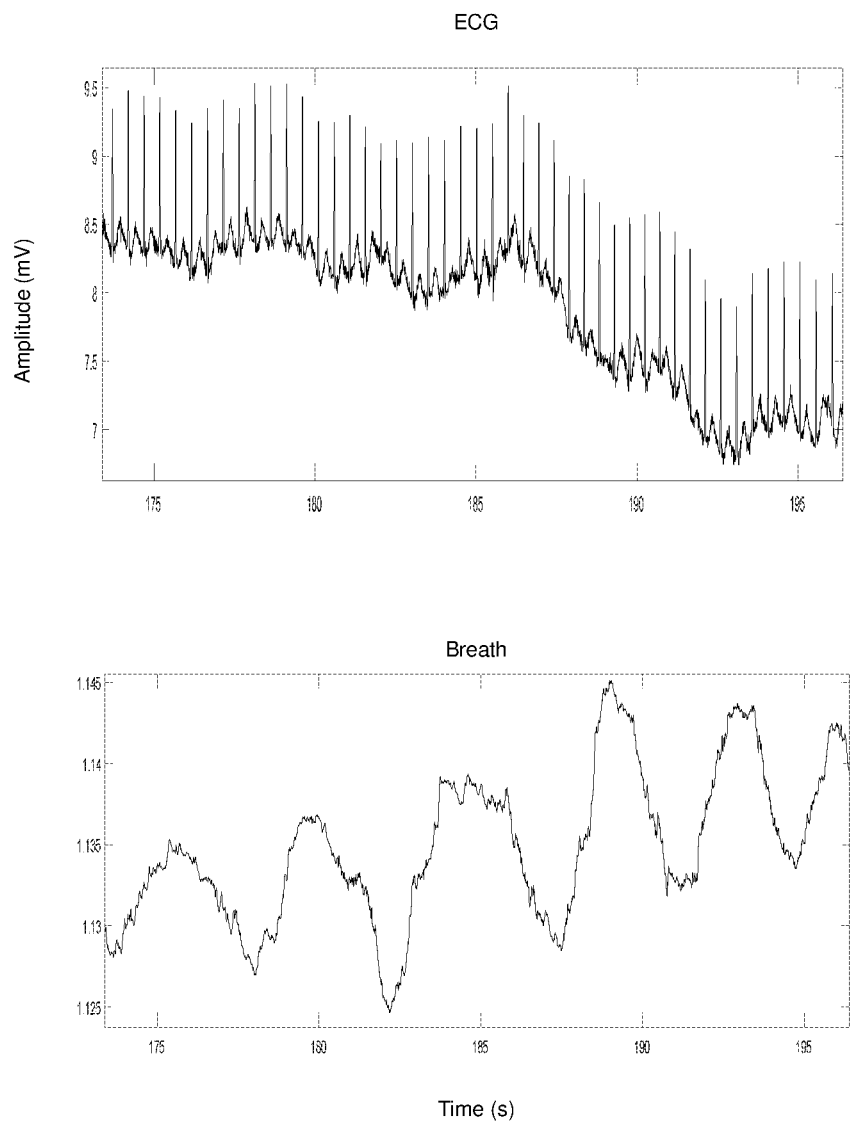
FIG. 21 shows the traces of ECG and BREATH (acquired with impedance technique from the same electrodes used for ECG, simultaneously) acquired on the same subject during moderate physical effort (pedaling).

Through the same reading electronics, same setup, on a healthy volunteer in pedaling activity with increasing intensity, several breath and ECG signals were detected simultaneously, through the same textile electrodes. The result is shown in:
1. FIG. 20: Subject who alternates breathing with apnea
2. FIG. 21: Subject during moderate physical effort.

In all cases there is a perfectly clean signal, despite the absence of any form of filtering (note the presence of normal low frequency and high frequency artifacts, which otherwise would not be present).

The invention claimed is:
1. A viscous conductive polymeric composition comprising PEDOT and one or more ionic liquids made by a process comprising:
(a) generating an aqueous suspension mixture comprising in % by weight:
a PEDOT conductive polymer in an amount between about 0.2 and 10%,
one or more ionic liquids in an amount between about 0.05-2.0%,
a secondary dopant in an amount between about 0-50%,
wherein the ratio (ionic liquid)/(PEDOT conductive polymer) is between about 0.5 and 15,
by mixing and heating the PEDOT conductive polymer, the one or more ionic liquids, and the secondary dopant, thereby generating an aqueous suspension mixture, and
(b) a first evaporating step comprising evaporating the water from the aqueous suspension mixture to generate a viscous aqueous suspension mixture comprising water in an amount between about 30% to about 99% by weight, wherein after the evaporating the aqueous suspension mixture has a viscosity of the mixture between about 100 and 10000 cP,
wherein each of the one or more ionic fluids comprises a compound having a general formula (I)

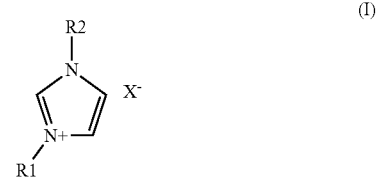

wherein
R1 and R2 independently of each other are branched or cyclic linear alkyl groups, with chain C1-C15,
X is an anion selected from alkylsulphates, tosylate, Ccarboxylates-i-Cs, such as formate and acetate, halides such as fluorides, chlorides, bromides and iodides, borates and phosphates, such as tetrafluoro borate and hexafluorophosphate, sulphonates.
2. The viscous conductive polymeric composition of claim 1, wherein the ionic liquids are selected from the group consisting of:
(a) 1-ethyl-3-methylimidazolium ethylsulphate (CAS: 342573-75-5),
(b) 1-butyl-3-methylimidazolium bromide (CAS number: 85100-77-2),
(c) 1-ethyl-3-methylimidazolium chloride (CAS number: 65039-09-0),
(d) 1-ethyl-3-methylimidazolium acetate (CAS number: 143314-17-4),
(e) 1-butyl-3-methylimidazolium acetate (CAS number: 284049-75-8),
(f) 1-ethyl-3-methylimidazolium tosylate (CAS number: 328090-25-1),
(g) 1-methyl-3-propylimidazolium iodide (CAS number: 1 19171-18-5),
(h) 1-decyl-3-methylimidazolium chloride (CAS number: 171058-18-7), and
(i) a mixture or any of (a) to (h) mixtures.
3. The viscous conductive polymeric composition of claim 1, wherein the ionic liquid comprises 1-butyl-3-methylimidazolium acetate, which is added in an amount of between about 0.1-2.0%.
4. The viscous conductive polymeric composition of claim 1, wherein PEDOT is salified with anions selected from the group consisting of: perchlorate, tetrafluoroborate, hexafluorophosphate, nitrate, sulphate, chloride, tosylate, sulphonamides with fluorinated substituents such as bis ((trifluoromethyl) sulphonyl)-amide, bis ((perfluoroethyl) sulphonyl) amide, bis ((heptafluoro-propinyl)-sulphonyl)

amide and bis ((nonafluoro-butinyl) sulphonyl) amide and sulphonates with fluorinated substituents, a triflate ion, nonafluorobuthane sulphonate and heptadecafluoroethane sulphonate.

5. The viscous conductive polymeric composition of claim 1, wherein PEDOT is salified with Polystyrene Sulphonate.

6. The viscous conductive polymeric composition of claim 1, wherein the secondary dopant is selected from: ethylene glycol, dimethylsulphoxide, dimethylformamide, methoxyethanol, diethylene glycol, dimethyl sulphate, xylitol, glycerol, sorbitol and meso-erythritol, and related mixtures.

7. The viscous conductive polymeric composition of claim 1, further comprising a cross-linker and a surfactant, either in an amount of between about 0.05-1.5% by weight.

8. A method for making a product of manufacture comprising an electrode, comprising the following steps:
(i) applying the viscous conductive polymeric composition of claim 1 to a surface of the product of manufacture; and
(ii) drying or evaporating the viscous conductive polymeric composition applied on the surface of the product of manufacture to reduce the amount of water in the viscous conductive polymeric composition as applied on the surface of the product of manufacture.

9. The method of claim 8, wherein:
(a) the drying or evaporating of the viscous conductive polymeric composition is stopped before a phase separation occurs between water and the PEDOT conductive polymer, the one or more ionic liquids and the secondary dopant of the aqueous suspension mixture; and/or
(b) the heating of the PEDOT conductive polymer, the one or more ionic liquids and the secondary dopant of the aqueous suspension mixture comprises heating the aqueous suspension mixture to a temperature of between about 40° C. and 100° C.

10. An electrode for recording bioelectric signals made by a method comprising:
(a) applying the viscous conductive polymeric composition of claim 1 to a surface of a product of manufacture; and
(b) drying or evaporating the viscous conductive polymeric composition applied on the surface of the product of manufacture to reduce the amount of water in the viscous conductive polymeric composition as applied on the surface of the product of manufacture.

11. The electrode of claim 10, wherein the electrode is operatively connected to a reading electronic of a device for detecting bioelectric parameters.

12. The electrode of claim 10, wherein the electrode has comprising the conductive polymeric composition a skin/electrode impedance lower than about 1000 kΩ measured at room temperature and about 20 Hz.

13. A device for detecting a bioelectric signal, wherein the device comprises a sensor comprising at least one electrode as set forth in claim 10.

14. The device of claim 13 wherein the bioelectronic signal comprises an electrophysiological signal from:
(a) a passive measurement selected from the group consisting of: electrocardiogram, electromyogram, electroneurogram, electroencephalogram, electrooculogram, and electrodermal activity; or
(b) an active measurement of electrodermal activity, bioimpedance, or breathing.

15. A product of manufacture comprising or having applied thereof an electrode of claim 10.

16. The product of manufacture of claim 15, fabricated as or comprising a rubber, a polyurethane foam, a fiber, a plastic film, a fabric, a textile or a material suitable for being placed in direct contact with epidermis.

17. The product of manufacture of claim 16, wherein the fabric comprises an elastic fabric or a non-woven fabric.

18. The product of manufacture of claim 15, fabricated as a T shirt, a sports shirt, a waterproof suit, a diving suit, a product of manufacture for use in a water sport or a submarine survey, a product of manufacture used in a medical or a sanitary field, a plaster, an elastic support band, an adhesive support band, a textile product, or a bioceramic fabric.

19. The viscous conductive polymeric composition of claim 1, wherein the heating of the PEDOT conductive polymer, the one or more ionic liquids, and the secondary dopant to generate an aqueous suspension mixture comprises heating between about 1 and 60 minutes at a temperature of between about 40° C. and 100° C.

20. The viscous conductive polymeric composition of claim 19, wherein the heating comprises a temperature of between about 50° C. and 70° C.

21. The electrode of claim 10, wherein the viscous conductive polymeric composition is applied to the surface of the product of manufacture by process comprising use of a printing technique or device.

22. The electrode of claim 21, wherein printing technique or device comprises a stencil, a brush and/or a screen printing device.

23. The electrode of claim 10, wherein the viscous conductive polymeric composition is applied to the surface of a textile, and the electrode is a textile electrode.

24. The electrode of claim 23, further comprising one or more contacts for connecting the textile electrode with an electronic unit for reading electrical signals recorded by the textile electrode electrode when t the textile electrode is placed in contact with skin.

25. The viscous conductive polymeric composition of claim 1, wherein R1 and R2 independently of each other are branched or cyclic linear alkyl groups, with chain C1-C10.

26. The viscous conductive polymeric composition of claim 12, wherein the electrode has a skin/electrode impedance lower than about 1000 kΩ measured at room temperature and between about 25 and 250 kΩ.

* * * * *